United States Patent [19]

Daly et al.

[11] Patent Number: 5,536,271
[45] Date of Patent: Jul. 16, 1996

[54] PATELLA REAMING SYSTEM

[75] Inventors: Anne M. Daly, Fort Wayne; Timothy J. Blackwell, Winona Lake; Troy D. Martin, Pierceton, all of Ind.

[73] Assignee: DePuy, Inc., Warsaw, Ind.

[21] Appl. No.: 252,885

[22] Filed: Jun. 2, 1994

[51] Int. Cl.$^6$ .................................................. A61B 17/56
[52] U.S. Cl. .................................. 606/80; 606/84; 606/88
[58] Field of Search ............................ 606/80, 79, 81, 606/82, 83, 84, 85, 88, 87, 86, 89, 96, 99, 102, 105; 623/18, 20; 408/3, 14, 15, 116, 189, 197, 198, 202, 203, 207, 224, 227, 241 G, 241 S

[56] References Cited

U.S. PATENT DOCUMENTS

| | | | |
|---|---|---|---|
| 3,867,932 | 1/1975 | Huene . | |
| 4,521,145 | 6/1985 | Bieler | 409/218 |
| 4,633,862 | 1/1987 | Petersen . | |
| 4,706,660 | 11/1987 | Petersen . | |
| 4,710,075 | 12/1987 | Davison . | |
| 4,964,867 | 10/1990 | Boger | 623/20 |
| 5,096,340 | 3/1992 | Forsgren | 408/14 |
| 5,108,401 | 4/1992 | Insall et al. | 606/79 |
| 5,116,338 | 5/1992 | Poggie et al. | 606/90 |
| 5,129,907 | 7/1992 | Heldreth et al. | 606/80 |
| 5,129,908 | 7/1992 | Petersen | 606/88 |
| 5,147,365 | 9/1992 | Whitlock et al. | 606/98 |
| 5,180,384 | 1/1993 | Mikhail | 606/80 |
| 5,222,955 | 6/1993 | Mikhail | 606/80 |
| 5,284,482 | 2/1994 | Mikhail | 606/86 |
| 5,295,992 | 3/1994 | Cameron | 606/79 |
| 5,342,364 | 8/1994 | Mikhail | 606/79 |

OTHER PUBLICATIONS

Brochure entitled: "Legend II Surgical Technique—The Concept of Personalization", 32 pages, copyright 1992, DePuy, Inc., Warsaw, IN, U.S.A. Author Unknown.
Brochure entitled: "Axiom Total Knee System", 8 pages, copyright 1992, Orthomet, Inc., Minneapolis, MN, U.S.A. Author Unknown.

*Primary Examiner*—Guy Tucker
*Attorney, Agent, or Firm*—Perman & Green

[57] ABSTRACT

A system is disclosed for preparing a natural patella for implantation of a patellar prosthesis. Substantially the same amount of bone removed from the natural patella is replaced by the prosthesis so that the reconstructed patella will replicate the natural one in diameter and thickness. To this end, the patella is held stationary and two operations are performed simultaneously. First, a posterior side of the patella is resected to form a prosthesis receiving surface for reception of a fixation surface of the patellar prosthesis. Second, a mounting bore is formed into the resected surface of the patella for reception of fixation members of the patellar prosthesis. A reamer is guided for movement between a first position spaced from the posterior surface of the patella and a second position in operative engagement with the patella at which formation of both the receiving surface and of the mounting bore therein has been completed. The reamer is stopped at the second position which is preselected according to the thickness of the patella such that the amount of the patella removed is substantially equal to the thickness of the patellar prosthesis.

18 Claims, 10 Drawing Sheets

FIG. 25 the present invention is directed to a system for preparing
PATELLA REAMING SYSTEM

BACKGROUND OF THE INVENTION

1. Field of the Invention

The present invention is directed to a system for preparing a human patella to receive a prosthesis and, thereafter, for implanting the prosthesis in the patella.

2. Description of the Prior Art

In total knee replacement surgery, a prosthesis is provided in which one component is fastened to the distal end of the femur which has been resectioned and another component is fastened to the proximal end of the tibia which has been resectioned so that the two components will act together in permitting the leg a full range of motion. In performing such surgery, the patella is not completely replaced but rather is resectioned such that the posterior dome portion facing the condyles is cut and reamed to form a cavity in which a patellar prosthesis is implanted. The patellar prosthesis has a dome facing inwardly to engage the patellar or trochlear groove of the femoral component.

Heretofore, in preparing a patella for an implant, it was necessary to firmly clamp the patella, perform a free hand resection using an oscillating saw, then ream a cavity in the patella of sufficient size to receive the patellar implant intended to be used. Depending upon a number of factors including the size of the patient, the patellar implant could be one of a number of different sizes. As a result of this, it was necessary to have available a number of guides, each having a different diameter, for guiding various size reamers. Typical prior art methods of forming a cavity for implanting a patellar prosthesis are shown and described in the following publication, which is incorporated herein by reference: a brochure entitled "Legend II Surgical Technique—The Concept of Personalization" copyright 1992, DePuy, Inc., Warsaw, Ind. A copy of this reference accompanies this disclosure.

Typically, a surgeon will select to install a patellar prosthesis by utilizing either (a) a resurfacing technique wherein the prosthetic patella will be positioned on the prepared surface of the patella or (b) an insetting technique wherein the prosthetic patella will be recessed or inset into the prepared surface of the patella. Accordingly, two varieties of guides could be available for connection to the patellar clamp and could be interchangeably connectable to the clamp. The interchangeable guides permit a surgeon to use the patellar clamp during either a total patellar bone surfacing procedure or a patella insetting procedure.

In either a total resurfacing procedure or a patella insetting procedure, it is important that a sufficient amount of bone stock remain after resection to accept the fixation means of the patellar prosthesis and maintain the integrity of the remaining patellar bone. If too much bone material is removed, the remaining patellar bone may be structurally weak.

In order to prevent an excessive amount of bone material from being resected, a prior art clamp and reamer included a stop ring carried by the shaft above the reamer blades. This type of stop controls the amount of bone removed from the patella, but does not control the minimum thickness of patella bone remaining. The stop ring engages with the upper surface of the reamer guide to stop the shaft and reamer from being further advanced into the patellar bone. A plurality of stop rings having a plurality of effective thicknesses may be interchangeably connected to the shaft of the reamer to accommodate the varying amount of bone to be resected as the thickness of the patellar bone varies between patients. The stop rings may be calibrated and may include measurement indicia thereon, in terms of the amount of bone material to be removed during resection. For example, if a surgeon needs to resect 10 mm of bone material, a ringed stop having the indication "10 mm", and correspondingly an effective thickness of 10 mm, would be turned onto the shaft. Therefore, the shaft and reamer would only be able to resect 10 mm of bone material before the stop ring engages the guide.

In a more recent development disclosed in U.S. Pat. No. 5,129,907 to Heldreth et al., an adjustable depth gauge wing is carried by the clamp and engaged by a collar on the reamer shaft. In this construction, the engagement of the collar and depth gauge wing prevents further movement of the reamer into the patella. The adjustable depth gauge wing includes a stepped upper surface having measurement indicia thereon which refer to distance in terms of the amount of patellar bone material to be left after resection. Four stepped levels are provided at 2 mm increments.

U.S. Pat. No. 4,964,867 to Boger and commonly assigned discloses a patellar prosthesis provided with a pair of concave protuberances for reception in an annular groove in a prepared resection of a natural patella. The instant invention might well utilize a prosthesis generally of this construction.

Another recent development, also commonly assigned, although not one specifically related to patellar prostheses is disclosed in U.S. Pat. No. 4,710,075 to Davison. The patented construction relates to a bone drill which provides a drill stop collar which can be selectively moved to and retained at a desired position along the length of a drill bit. When the stop collar engages the surface of the bone, axial movement of the drill bit ceases.

SUMMARY OF THE INVENTION

It was in light of the prior art as just discussed that the present invention was conceived and has now been reduced to practice. Consistent with the dome shape of the natural patella, the AMK® patella implants provided by DePuy Inc. of Warsaw, Ind. are also dome shaped. Consequently the thickness varies with the diameter. Area coverage is paramount when reconstructing the patella and the thickness of bone resected may be changed to maximize area coverage. The philosophy behind the AMK® patella reaming system of the invention is to replace the same amount of bone that is removed so that the reconstructed patella will replicate the natural one in diameter and thickness. In other words, the amount of bone removed from the patella is equal to the amount of polyethylene material replacing it. This will provide a reconstructed patella with the same thickness as the natural patella which will allow normal patella tracking and knee kinematics. Therefore the patellar diameter determines the size of the implant for maximum area coverage and the thickness is dictated from that. The AMK® patella implants, which are typical, are outlined in the table below.

TABLE 1

AMK Patella Implant Dimensions

| Diameter (mm) | Thickness (mm) |
|---|---|
| 30 | 7.5 |
| 34 | 8.5 |
| 38 | 9.5 |
| 40 | 10 |

In order to receive a patellar implant, a patient is prepared for surgery and the knee is surgically exposed in the normal manner. The everted patella thickness and diameter are measured with a patella caliper and patella sizer, respectively. Once the patella size (diameter) is determined, a reamer depth stop ring is placed onto the shaft of that sized reamer before the reamer is attached to the power equipment. The surgeon sets the depth stop at the measured thickness. Indicia lines on the reamer shaft are 2 mm apart in even millimeter increments and indicia numbers are 4 mm apart in even millimeter increments. A resection depth for odd numbers, say 19 mm, would therefore be set between the line marked 20 mm and the line corresponding to 18 mm which is not numbered.

If the patella measures 28 mm thick initially and a 38 mm diameter implant will be used, there will be 9.5 mm of bone removed from the anterior face of the patella. The patella implant will then add the 9.5 mm back and the reconstructed patella will measure 28 mm thick.

A depth gauge tower is secured to the lower jaw of the patella clamp and an appropriately sized bushing is attached to the upper jaw of the patella clamp. The patella is grasped firmly in the patella clamp so that the posterior surface to be resected protrudes into the bushing.

The reamer, with the depth stop ring already set, is placed in the bushing with the shaft of the reamer between U-shaped prongs of the depth gauge tower. The surgeon reams the patella until the depth stop ring rests on the depth gauge tower. The surgeon may then check the depth of resection and remove more bone if desired by raising the depth stop ring additional millimeters and repeating the above steps. The "depth of resection" refers to the amount of bone removed from the posterior face of the patella and does not include the additional depth of the center groove.

The depth gauge tower of the invention references off of the anterior face of the patella which maintains a constant distance between the bottom jaw of the clamp and the depth gauge arms. As a result, the reamer is the only component that moves and the length of the reamer below the depth gauge arms is the only way to know the thickness. The AMK® patella reaming system, therefore, results from the philosophy of removing only the amount of bone that will be replaced so that the reconstructed patella will be the same thickness as the anatomical patella.

AMK® patella implants include a ring that protrudes from the anterior side of the implant for fixation in the bone and cement. This ring provides a more stable cement fixation than do pegs or posts. Previously, the patella had to be resected with an oscillating saw by hand at the patellar tendon level and the cement fixation interface was placed into the bone bed by whatever means the manufacturer supplied. With the previous AMK® system reamers were used to plane the resected surface and add the cement fixation groove. While other manufacturers have introduced patella preparation systems to eliminate the free-hand resection step, such cement interfaces are either pegs or posts and need to be added after the planing process. With the system of the invention, the groove to accept the ring is prepared in the bone bed during the reaming process.

Thus, only the system of the invention is a truly one-step system because of the configuration of the cement interface of the implant. All other known systems may ream in a single step but they still require additional bone preparation to accept the fixation interface.

In short, then, the system of the invention allows the surgeon to clamp the patella bone, set the desired depth of resection based on the implant size; and resect, ream, and prepare the implant bed, all in one easy step.

The system comprises one reamer for each size patella implant, a patella clamp which can be used for all sizes of implants, one locking ring that mates with all of the reamer shafts, and one depth stop that attaches to the patella clamp. The patella reamer shaft is equipped with holes one millimeter apart for accurately setting patella resection depth. The locking ring is adjusted by depressing a button and sliding the ring along the shaft to the desired depth of resection and locks easily by releasing the button. The surgeon then reams until the locking ring contacts the depth stop and the patella is ready for implantation. This system is much less cumbersome than known patella revision systems and allows the surgeon to set the amount of bone removed.

As noted above, one known system has four predetermined depths of resection, but these cannot be further adjusted. With this known system, a surgeon must choose one of these four thicknesses which may be four or five millimeters different than the original patella. This does not really provide for an anatomic reconstruction. With the system of the invention, however, the surgeon may select a thickness that most closely approximates the original patella within one half millimeter.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention and, together with the description, serve to explain the principles of the invention in general terms. Like numbers refer to like parts throughout the disclosure.

DETAILED DESCRIPTION OF THE PREFERRED EMBODIMENT

Figure 1:
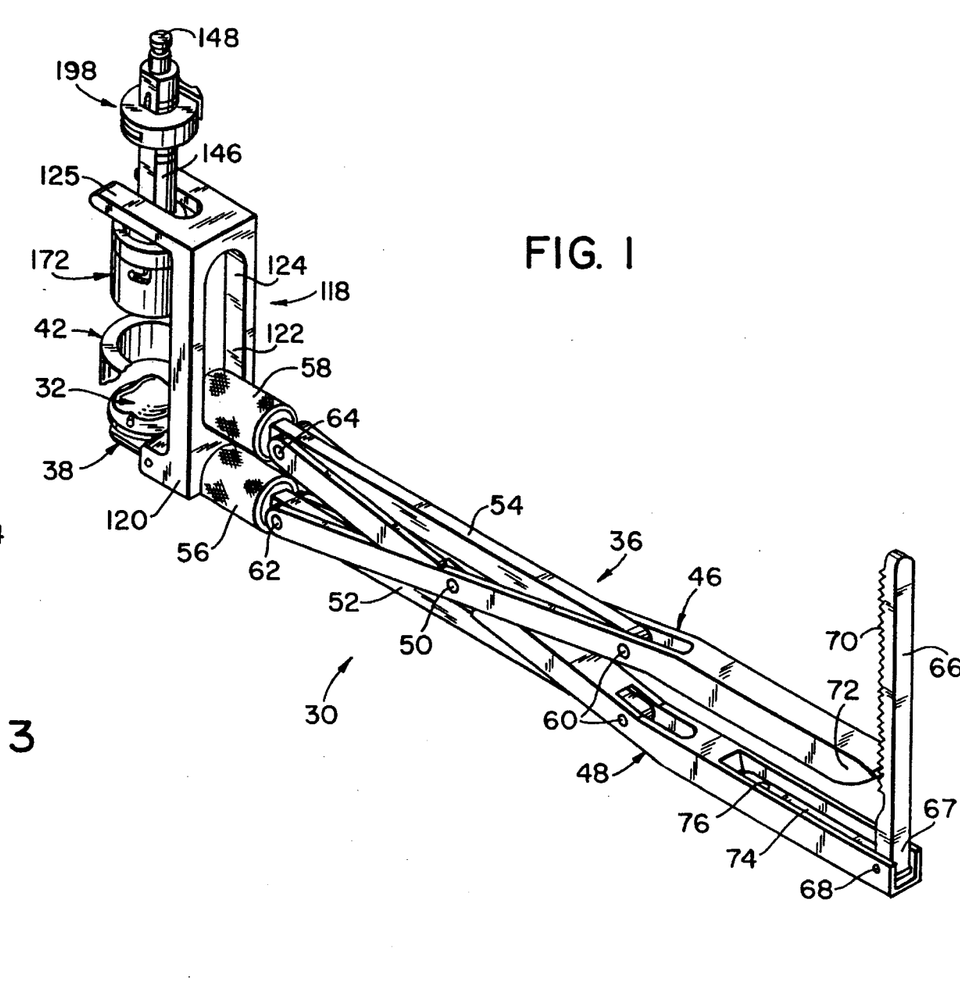
FIG. 1 is a perspective view of a patella reaming system embodying the present invention.
Figure 2A:
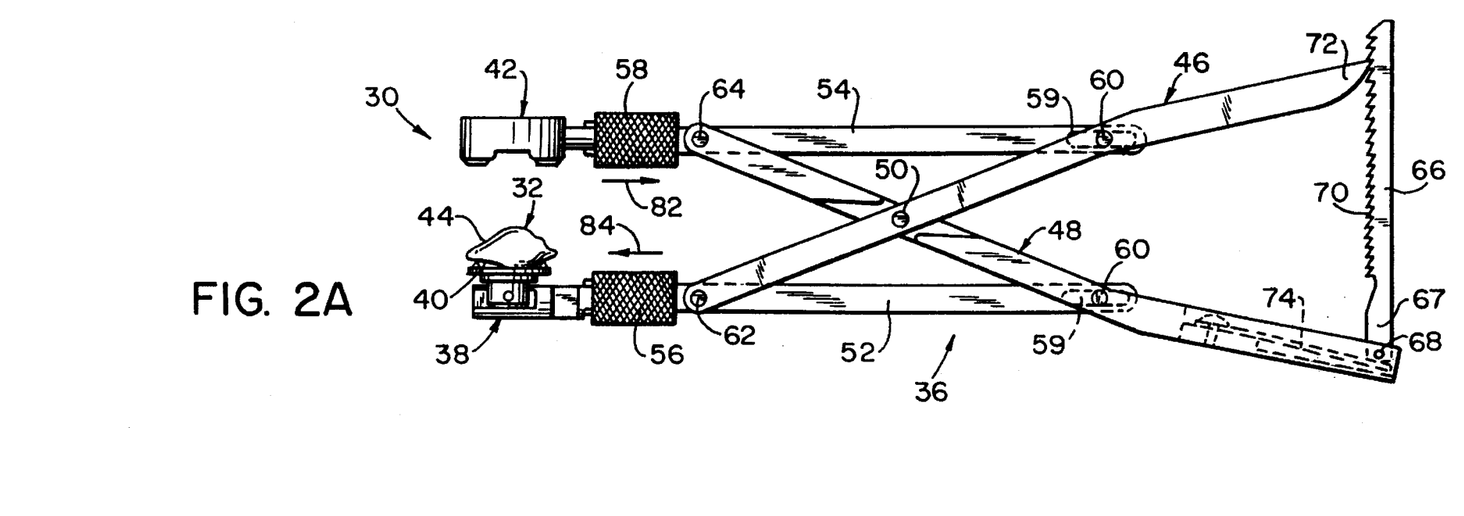
FIGS. 2A and 2B are side elevation views of a part of the system illustrated in FIG. 1 depicting, respectively, open and closed positions of a patellar clamp.
Figure 2B:
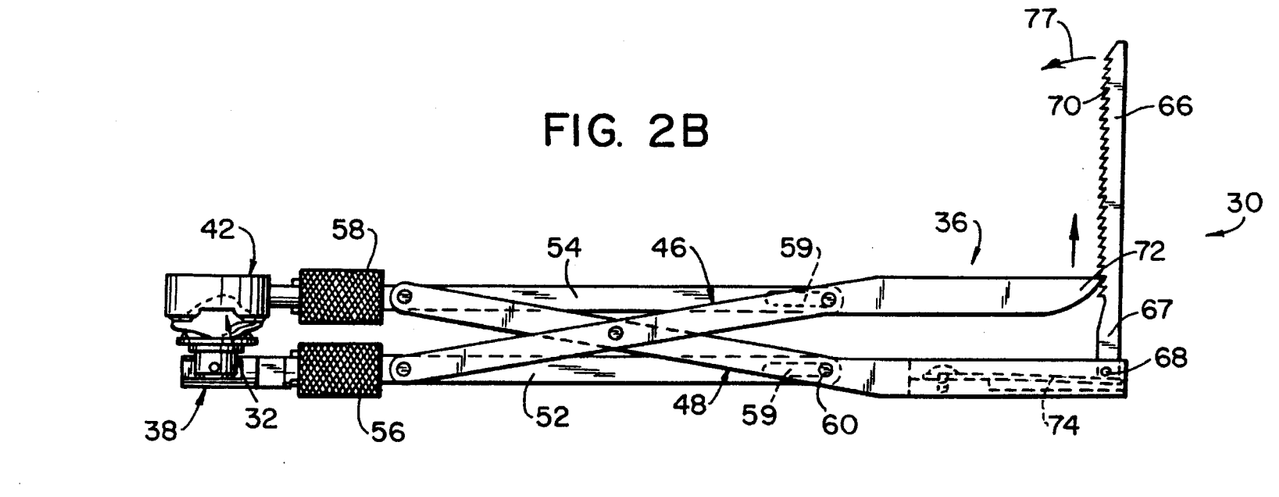

Turn now to the drawings, and initially, to FIGS. 1, 2A, and 2B which illustrate apparatus 30 for preparing a natural patella 32 (see FIG. 3) for implantation thereon of a patellar prosthesis 34.

The apparatus 30 includes a support mechanism in the form of a patellar clamp 36. The patellar clamp utilizes a linkage which operates a first jaw mechanism 38 for engaging an anterior surface 40 of the patella 32 (FIG. 2A) and a second jaw mechanism 42 for engaging a posterior surface 44 of the patella. The patellar clamp 36 is of such a construction, as will be explained, that the jaw mechanisms 38 and 42 remain aligned on a common axis as they are moved between an open position (FIG. 2A) for freely receiving the patella therebetween and a closed position (FIG. 2B) in engagement with the patella to hold it stationary.

The patellar clamp 36 includes a first handle 46 for releasably mounting the first jaw mechanism 38 and a second handle 48 for releasably mounting the second jaw mechanism 42. The handles 46, 48 are pivotally joined at a pin 50. The patellar clamp 36 also includes a pair of parallel, spaced apart, links 52, 54. A first link 52 mounts a first connector 56 at one end and, similarly, a second link 54 suitably mounts a second connector 58 at an adjacent end.

The ends of the links 52, 54 opposite the connectors 56, 58, respectively, are formed with elongated slots 59, each slidably receiving a pin 60 fixed, respectively, to the handles 46, 48. Extremities of the handles 46, 48 are pivotally connected, as at 62, 64, to the links 52, 54, respectively, adjacent the connectors 56, 58.

A locking mechanism will now be described for selectively locking handle 46 against movement relative to handle 48 at any one of a plurality of positions. This locking mechanism includes a handle ratchet 66 which is an elongated member pivotally mounted at a terminal end 67 to the handle 48 by means of a pin 68. The handle ratchet 66 is formed with a plurality of longitudinally spaced teeth 70 which are positioned for engagement by a projection member 72 at an extremity of the handle 46. A longitudinally extending leaf spring 74 is fixedly mounted within a longitudinally extending recess 76 within the handle 48 at an end distant from the jaw mechanism 42. The spring 74 operates to bias the handle ratchet 66 in a counter clockwise direction (see arrow 77, FIG. 2B), viewing FIGS. 1, 2A, and 2B, and into engagement with the projection member 72.

A surgeon or other operator handling the apparatus 30 can readily disengage the teeth 70 from the projection member 72 by pivoting the handle ratchet 66 in the clockwise direction (FIGS. 1, 2A, 2B). The apparatus 30 can then be opened to a position as indicated in FIG. 2A for placement of the patella 32 onto the jaw mechanism 38. Thereafter, the surgeon need only draw the handles 46, 48, together so that they assume a clamping position, as illustrated in FIG. 2B, with the patella 32 firmly held between the jaw mechanisms 38, 42. The natural tendency is for the handle ratchet 66 to pivot in the direction of arrow 77 until the teeth 70 again engage the projection member 72 and hold the handles 46, 48 fixed relative to one another.

Figures 4, 5, 12:
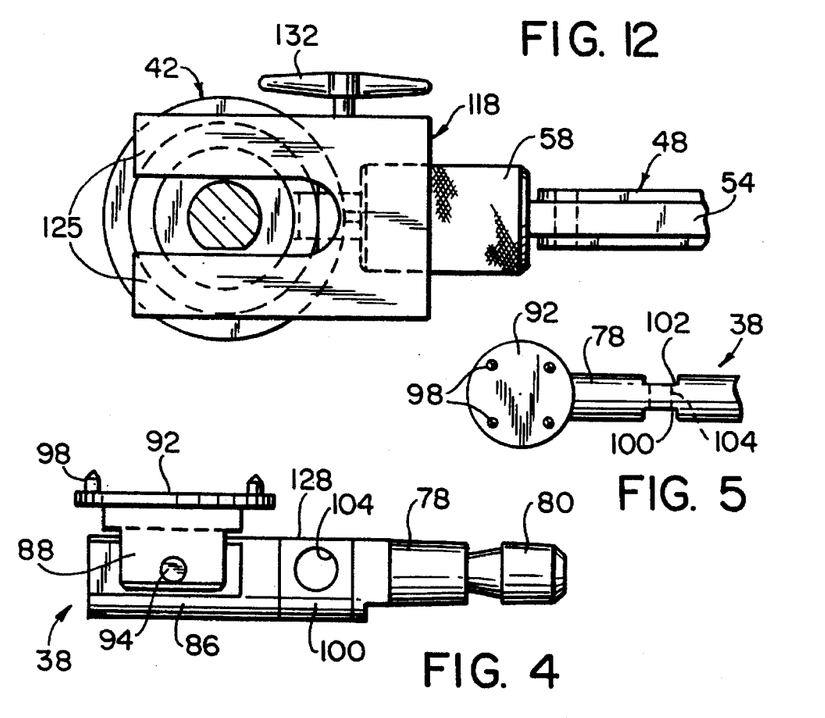
FIG. 4 is a side elevation view, partly broken away, of one jaw mechanism of the invention.
FIGS. 5 and 6 are detail top and front elevation views, respectively, illustrating the jaw mechanism of FIG. 4.
FIG. 12 is a cross-section view taken generally along line 12—12 in FIG. 11.
Figure 6:
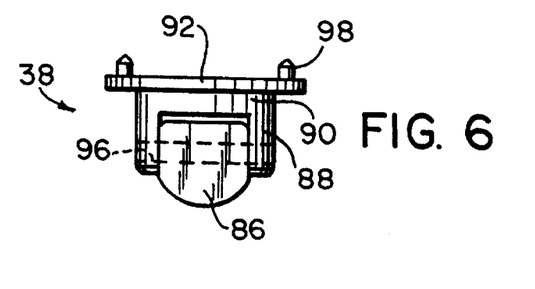

Turn now to FIGS. 4, 5, and 6 for a description of the first jaw mechanism 38. As seen therein, the jaw mechanism 38 has a first mounting finger 78 which includes a mounting end 80 for selective insertion into the first connector 56 for releasable attachment thereto. Each of the connectors 56, 58 may be of a well known variety of connectors such as those referred to as "hudson" connectors. As is typical of this type of connector, when moved to the right as indicated by an arrow 82 in FIG. 2A, the connectors 56, 58 are caused to open internally so as to receive the mounting end 80. Subsequently, when moved to the left, viewing FIG. 2A, as indicated by an arrow 84, the internal mechanism is caused to close and firmly grip the mounting end 80. Such connectors are well known and the specifics of their internal mechanism form no part of the present invention. The jaw mechanism 38 further includes a mounting block 86 which is integral with the mounting finger 78 and serves to freely receive opposed ears 88 which project downwardly from a base 90 of a support plate 92. The base 90 is pivotally mounted to the block 86 by a pin 94 which projects from the base 90 and is freely received in opposed aligned bores 96 formed in the opposed ears 88. A plurality of gripping members 98 project away from a mounting surface of the support plate 92 for gripping engagement with the anterior surface 40 of the patella 32. The mounting finger 78 is also formed with a pair of opposed recesses 100, 102 (FIG. 5), intermediate its ends, for a purpose to be explained subsequently. A cross bore 104 extends through the mounting finger 78 at the region of the recesses 100, 102.

Figure 7:
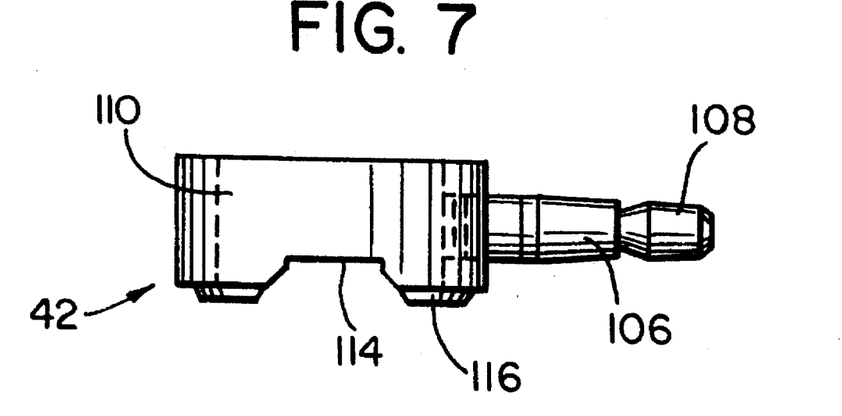
FIGS. 7 and 8 are detail side elevation and top plan views, respectively, of another jaw mechanism of the invention.
Figure 8:
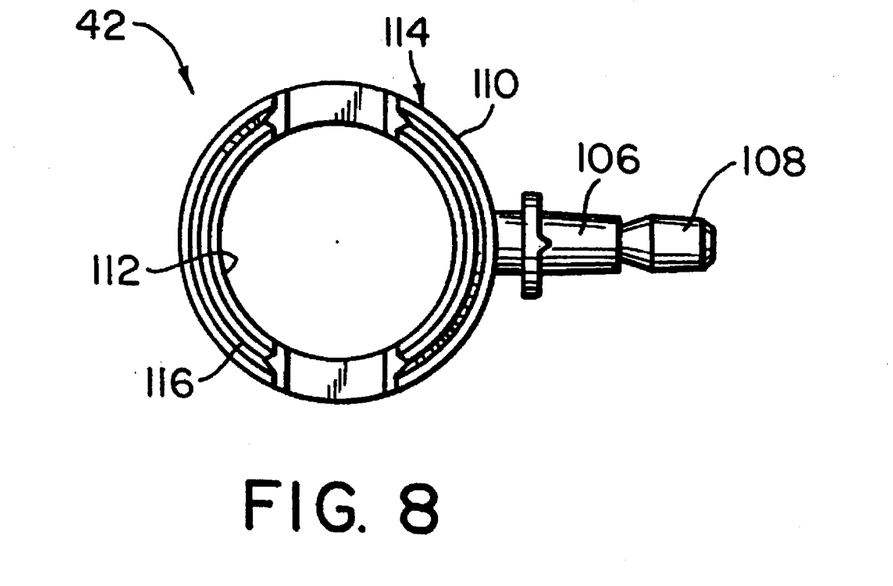

Turn now to FIGS. 7 and 8 for a description of the second jaw mechanism 42. In a manner very similar to that of the jaw mechanism 38, the jaw mechanism 42 includes a second mounting finger 106 which has a mounting end 108 for selective insertion into the second connector 58 for releasable attachment thereto. An annular bushing 110 is integral with the mounting finger 106 at an end opposite the mounting end 108 such that the mounting finger is aligned with a diameter of the bushing and is co-planar with the bushing. The bushing 110 is formed with a guide bore 112 whose function will be described below. The bushing 110 is also formed with an annular under surface 114 from which a pair of arcuate gripping members 116 project for gripping engagement with the posterior surface 44 of the patella 32.

Figures 9, 10:
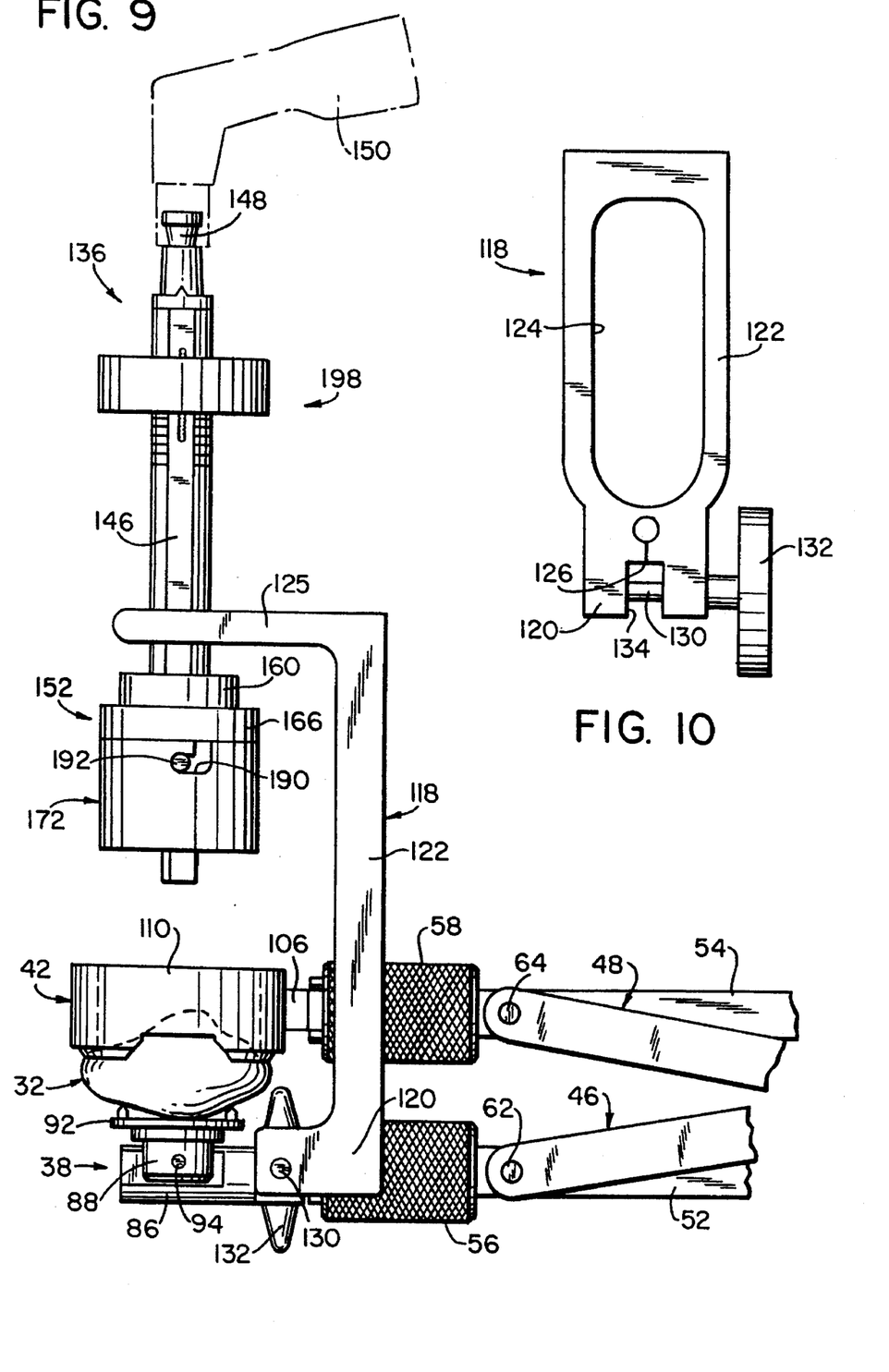
FIG. 9 is a detail side elevation view of the system illustrated in FIG. 1.
FIG. 10 is a rear elevation view of a component, a depth gauge tower, illustrated in FIG. 9.

With reference now to FIGS. 9 and 10, a depth gauge tower 118 is illustrated which is adapted to be releasably mounted on the jaw mechanism 38. The tower 118 includes a bifurcated base member 120 (FIG. 10), a main body 122 defining an interior window 124, and, distant from the base member 120, a pair of spaced apart substantially parallel prong arms 125 (FIGS. 1 and 12). The prong arms 125 are integral with the main body 122 and extend transversely therefrom for a purpose to be described below.

The tower 118 is attached to the jaw mechanism 38 by placement of the base member 120 into sliding engagement with the opposed recesses 100, 102 of the mounting finger 78. When a terminal surface 126 (FIG. 10) of the bifurcated base member 120 engages an upper surface 128 (FIG. 4) of the mounting finger 78, a mounting pin 130 is aligned with the cross bore 104 in the finger 78. A handle 132, rotatably mounted on the base member 120 operates the mounting pin 130 to retract it from a slot 134 in the base member and, thereafter, to advance it through the cross bore 104 to firmly mount the tower 118 on the jaw mechanism 38. It will be appreciated that the dimensions of the base member 120 and of the recesses 100, 102 are chosen to assure a firm mount for the tower. It will also be appreciated that the window 124 is positioned for reception therethrough of the connector 58 and is of sufficient height to accommodate the connector 58 throughout the range of positions it may assume as the jaw mechanisms 38, 42 are moved between open and closed positions as depicted by FIGS. 2A and 2B, respectively.

Although the tower 118 has been described as being removably mounted on the jaw mechanism 38, it is within the scope of the invention for it to be fixed to the jaw mechanism.

Figure 11:
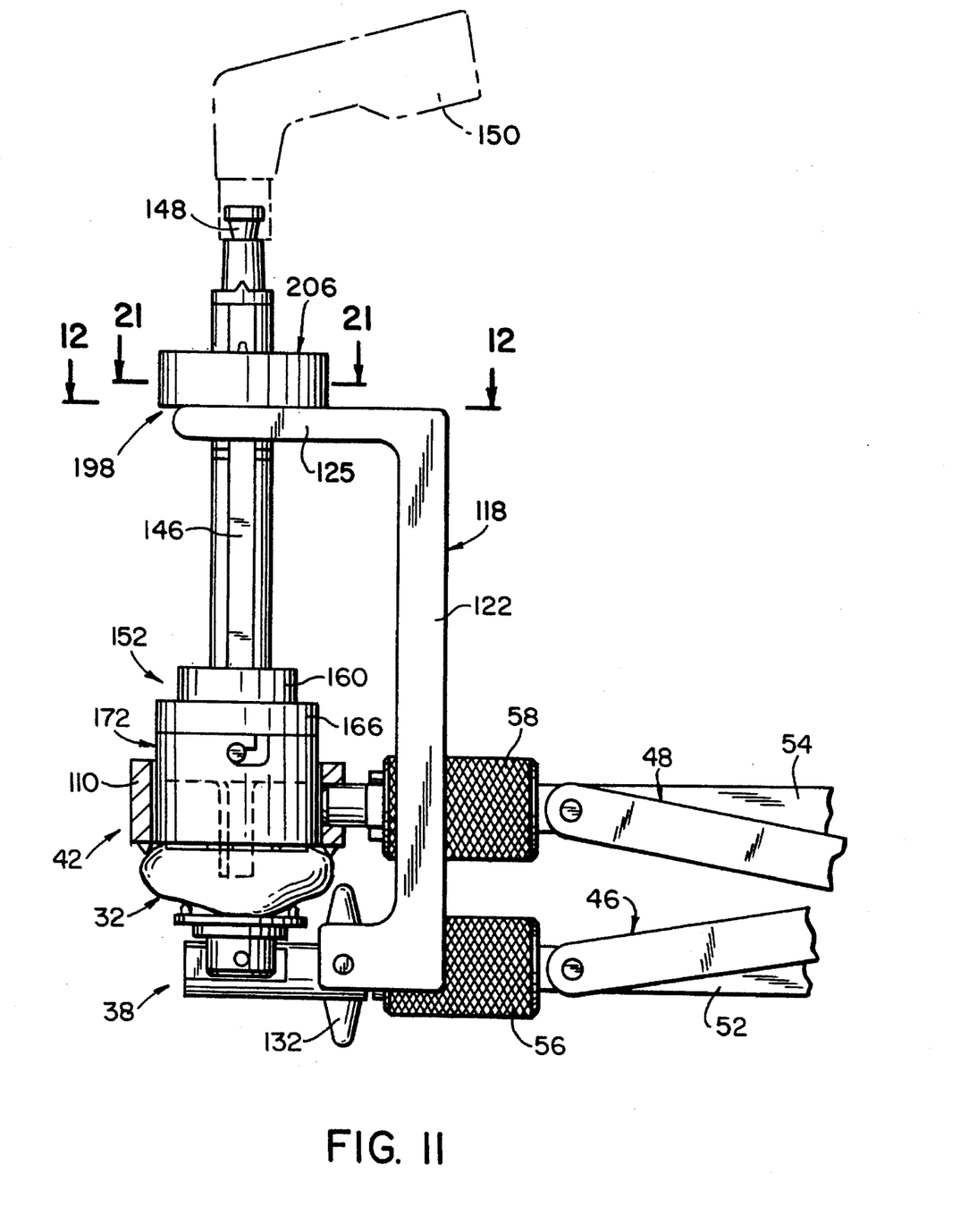
FIG. 11 is a detail side elevation view, similar to FIG. 9, but illustrating another position of the components therein.

A reamer assembly 136 will now be described with particular reference to FIGS. 9 and 13–18. The reamer assembly serves to simultaneously resect the posterior surface 44 of the patella as it is held by the jaw mechanisms 38, 42 to thereby form a prosthesis receiving surface 138 (FIG. 3) for reception thereon of a fixation surface 140 of the patellar prosthesis 34. Simultaneous with the resecting operation, an annular mounting bore 142 (FIG. 3) is formed for mating reception of an annular fixation member 144 which projects away from the fixation surface 140 of the patellar prosthesis 34. The reamer assembly 136 is movable between an initial, withdrawn, position adjacent to the posterior surface of the patella as illustrated in FIG. 9 and an advanced position as illustrated in FIG. 11 at which formation of both the receiving surface 138 and of the mounting bore 142 has been completed.

Figure 3:
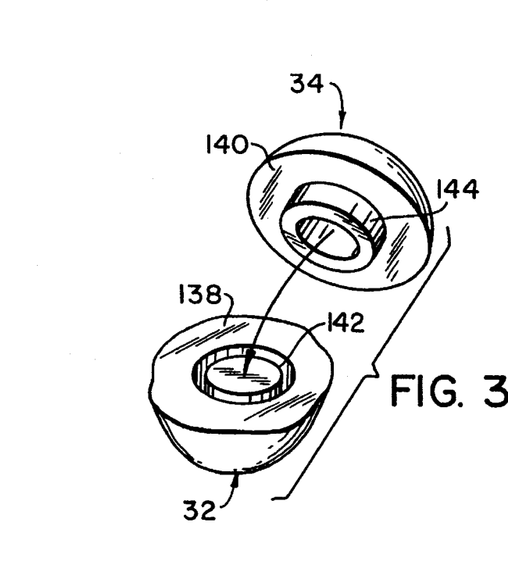
FIG. 3 is a detail exploded perspective view illustrating a resected patella and a prosthesis intended to be implanted thereon.
Figure 13:
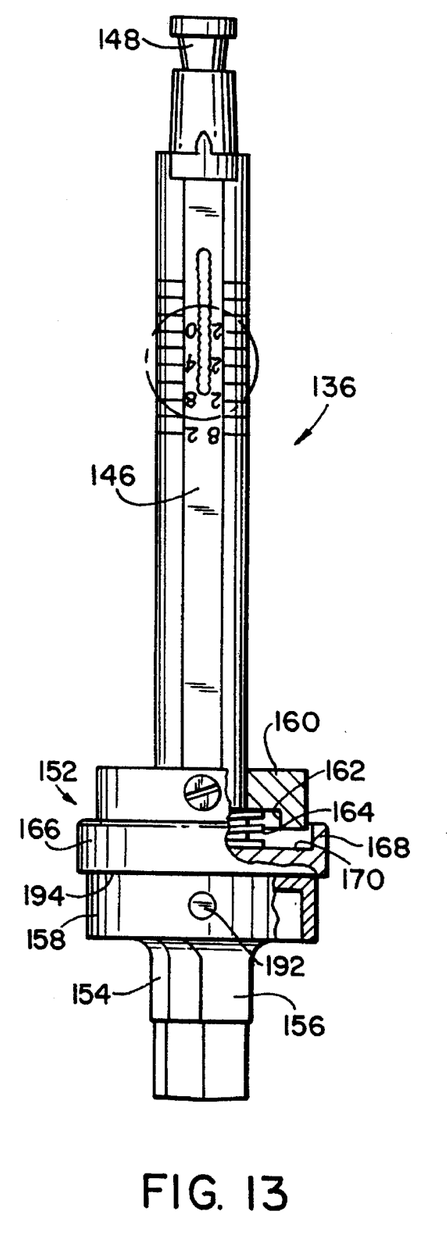
FIG. 13 is a detail side elevation view of a reamer driver used with the patella reaming system of FIG. 1.
Figure 14:
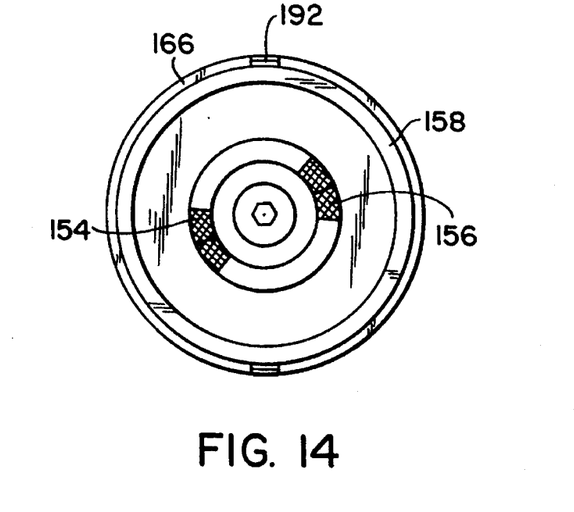
FIG. 14 is an end view of the reamer driver illustrated in FIG. 13.

The reamer assembly 136 includes an elongated shaft 146 which extends between a driving end 148 intended for driving engagement with a chuck of a suitable drive motor 150 and a driven end 152 distant from the driving end. The driven end 152, as seen particularly well in FIGS. 13 and 14, includes a pair of opposed arcuate cutter blades 154, 156 for forming the annular mounting bore 142 in the patella 32 (FIG. 3). The cutter blades 154, 156 are integral with the shaft 146 and are encompassed by an integral rim 158 located a distance from the extremities of the blades. Still farther distant from the extremities of the cutter blades 154, 156 is a collar 160 also fixed to the shaft 146. The collar 160 is recessed as at 162 so as to receive, coaxial of the shaft 146, a compression spring 164. A press plate 166 with an annular rim 168 is mounted between the rim member 158 and the collar 160 and supports an end of the helical spring 164 opposite the end which bears against the collar 160. The annular rim 168 straddles the outer peripheral surface of the collar 160. When the spring 164 is fully extended, the relative positioning of the collar 160 and of the press plate 166 is as indicated in FIG. 13. However, when the press plate 166 is moved longitudinally of the shaft 146 so that an internal surface 170 engages the collar 160 compressing the spring 164, the annular rim 168 advances so that it partially overlies the outer surface of the collar 160.

The purpose for the construction just described is to accommodate the mounting onto the rim member 158 of a patellar basket 172 in a manner to be described. Viewing especially FIGS. 16, 17, and 18, the patellar basket 172 includes a cylindrical sidewall 174, a bottom wall 176, and resection cutting blades 178, 180 integral with the bottom wall. Adjacent openings 182, 184, are associated, respectively, with the cutting blades 178, 180. The openings 182, 184 serve specifically to receive and pass into the interior of the patellar basket 172 bone material excised from the patella upon operation of the reamer assembly 136 in a manner to be described in greater detail below, and, broadly, to effect formation of the prosthesis receiving surface 138 as illustrated in FIG. 3. The bottom wall 176 is also formed with a pair of arcuate openings 186 concentric with a longitudinal axis of the patellar basket 172 for reception therethrough of the cutter blades 154, 156.

Adjacent an uppermost peripheral edge 188, are a pair of diametrically opposed J-shaped slots 190 which are sized and shaped for interengagement with a pair of radially protruding mounting pins 192 at diametrically opposite locations on the rim member 158. The slots 190 and mounting pins 192 are in the nature of a bayonet mount. More specifically, the patellar basket 172 is applied to the driven end 152 of the reamer assembly 136 such that the cutter blades 154, 156 protrude through the arcuate openings 186 in the bottom wall 176. Thereupon, the uppermost peripheral edge 188 of the patellar basket 172 comes into engagement with a mating lowermost surface 194 on the press plate 166. In order for this to be achieved, the mounting pins 192 must be aligned with those portions of the J-shaped slots 190 which intersect with the uppermost peripheral edge 188. As force continues to be applied to the patellar basket 172 in the direction of the driving end 148 of the shaft 146, the press plate 166 is moved in the direction of the driving end 148 and the spring 164 is compressed. When the surface 170 engages the collar 160, the patellar basket 172 is then rotated until the mounting pins 192 engage extreme portions 196 of the slots 190. At this point, when the surgeon or operator releases the collar 160, the spring 164 moves to a slightly extended configuration thereby holding the mounting pins 192 in firm engagement with the extreme portions 196 of the slots 190. The spring rate of the spring 164 is of sufficient magnitude to enable the resection cutting operation to be performed in the manner which will be described below.

With the patella 32 held stationary by the jaw mechanisms 38, 42 as illustrated in FIG. 9, the reamer assembly 136 is advanced in the direction of the patella until the resectioning and cutting operations have been completed as illustrated in FIG. 11. In order for such operations to occur, the shaft 146 is positioned between the prongs 125 and the patellar basket 172 is aligned with the annular bushing 110 so as to be slidably received by the guide bore 112 therein. In this manner, the annular bushing 110 serves as a guide for the cutter blades 154, 156 and for the resection cutting blades 178, 180 as they approach, then engage, the posterior surface 44 of the patella 32.

Figure 15:
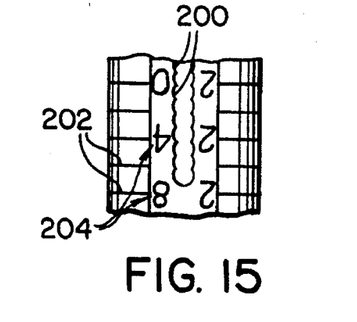
FIG. 15 is a detail view of the circled region indicated in FIG. 13.
Figure 16:
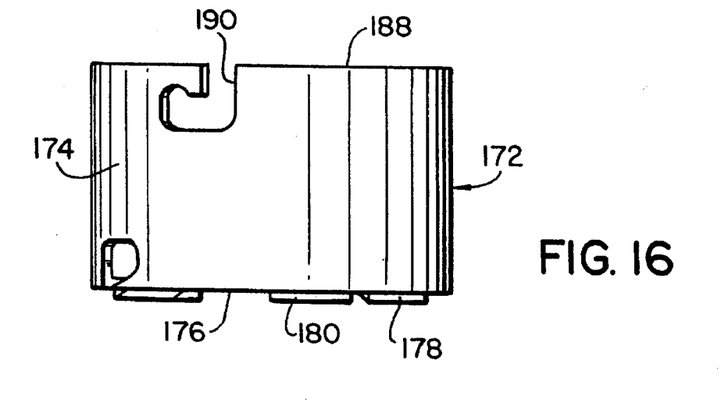
FIG. 16 is a side elevation view of a reamer basket employed by the patella reaming system of FIG. 1.
Figure 17:
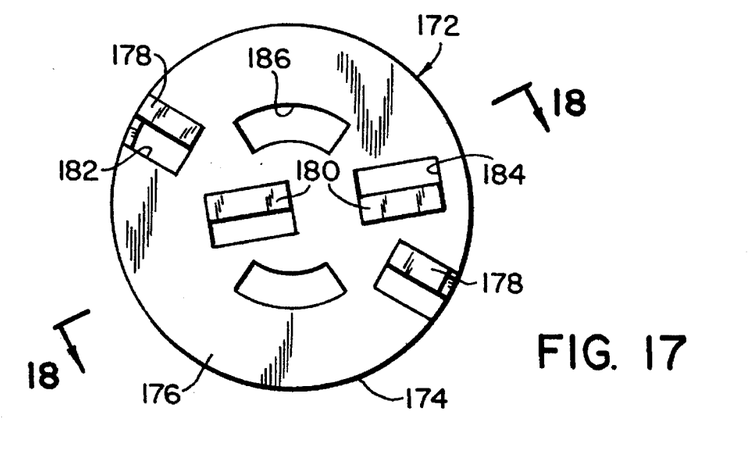
FIG. 17 is a bottom view of the reamer basket illustrated in FIG. 16 as mounted on the reamer driver illustrated in FIG. 13.
Figure 18:
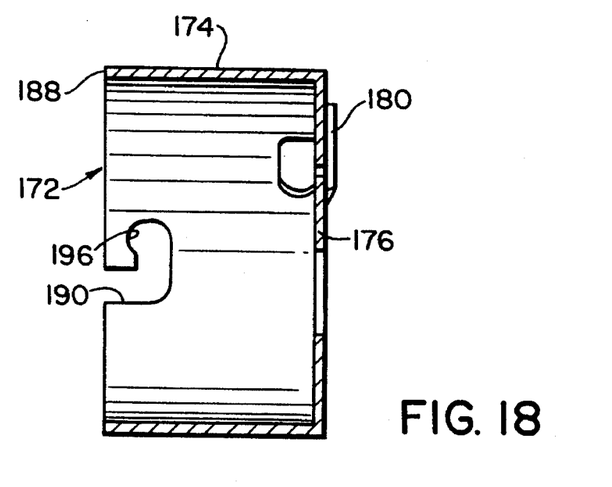
FIG. 18 is a cross-section view taken generally along line 18—18 in FIG. 17.

A stop assembly 198 is provided for stopping the driven end 152 in a predetermined manner such that the depth of resection of the patella 32 is substantially equal to the thickness of the selected patellar prosthesis. In this manner, it is assured that the reconstructed patella will have the same total thickness as the original natural patella. Some distance away from the driving end 148 are a plurality of longitudinally spaced transversely formed holes 200 which are nominally 1 mm apart (FIG. 15). A plurality of longitudinally spaced, laterally extending, indicia lines 202 may be nominally formed at 2 mm intervals, and indicia numbers 204 may be engraved, for example, at 4 mm intervals. The indicia lines 202 and indicia numbers 204 serve to indicate the depth of the resection to be performed.

Turn now especially to FIGS. 19, 20, 21, 22, and 23 for a description of a stop member 206 which is a component of the stop assembly 198. The stop member 206 includes a stop ring 208 which has upper and lower spaced walls 210, 212 with aligned upper and lower central apertures 214, 216 therein. The apertures 214,216 are provided to slidably receive the shaft 146 extending therethrough. A peripheral wall 218 joins the upper and lower walls 210, 212 and all of the walls define an internal cavity 220. An opening 222 is formed in the peripheral wall 218 to enable entry into the internal cavity 220. An operator button 224 includes a tongue 226 which is shaped and sized for slidable reception through the opening 222 into the internal cavity 220. The tongue 226 has a central bore 228 therethrough which is coincident with the upper and lower apertures 214, 216 in the upper and lower walls 210, 212 when the tongue is fully received in the internal cavity. A locking pin 230, integral with the tongue 226, projects into the central bore 228. The operator button 224 is movable between a locking position (FIG. 21) at which the central bore 228 is coincident with the upper and lower apertures 214, 216 and a release position (FIG. 20) at which the locking pin 230 is retracted from a position coincident with the upper and lower apertures. When the stop member 206 is received on the shaft 146, the locking pin 230 is selectively receivable in any one of the stop holes 200 therein.

Figures 19, 20, 22, 23:
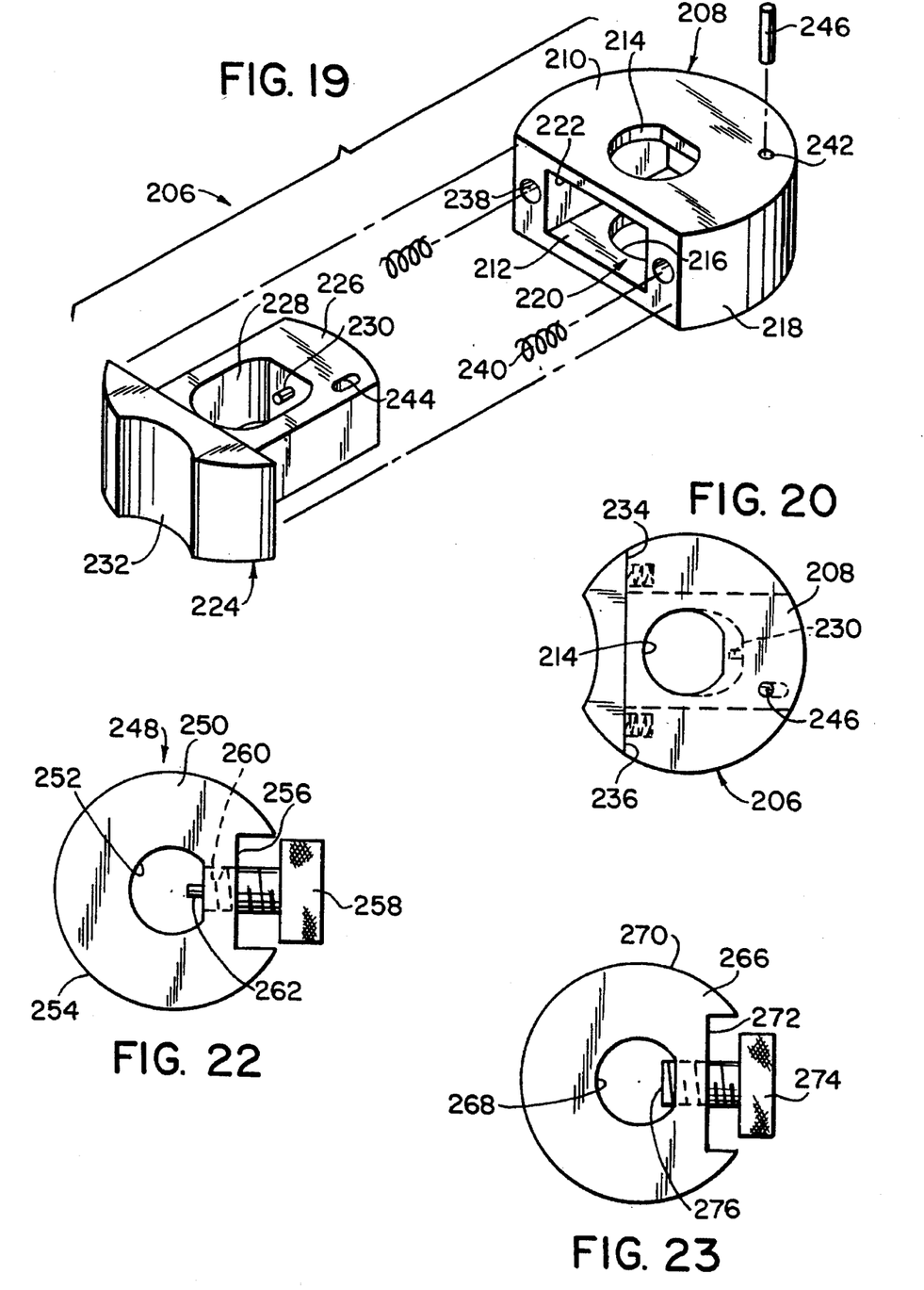
FIG. 19 is an exploded perspective view of a depth stop ring utilized with the patella reaming system of FIG. 1.
FIG. 20 is a top plan view of the depth stop ring illustrated in FIG. 19, depicting one relative position thereof.
FIG. 22 is a top plan view, similar to FIG. 20, illustrating another embodiment of the depth stop ring illustrated in FIGS. 19–21.
FIG. 23 is a top plan view, similar to FIGS. 20 and 22, depicting yet another embodiment of the depth stop ring illustrated in FIGS. 19–21.
Figure 21:
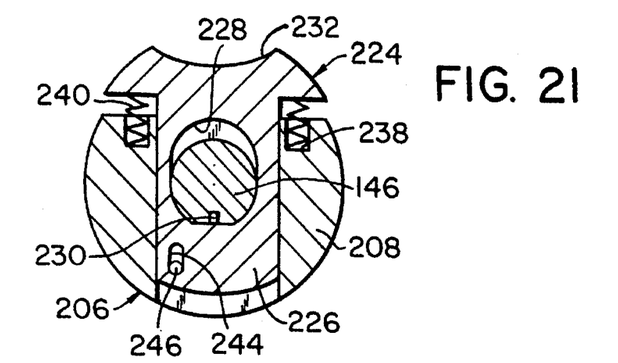
FIG. 21 is a detail cross-section view, taken along line 21—21 in FIG. 11, of the depth stop ring illustrated in FIGS. 19 and 20 and depicting another relative position thereof.

The operator button 224 also includes a press knob 232 intended to be engaged by the thumb or finger of the surgeon or other operator of the apparatus 30. A back side of the press knob 234 is provided with a pair of spaced spring engaging surfaces 234,236 (FIG. 20). The stop ring 208 has a pair of spaced apart spring receiving bores 238 in the peripheral wall 218, to either side of the opening 222 and generally aligned with the spring engaging surfaces 234, 236. A pair of compression springs 240 are received, respectively, in the spring receiving bores 238. With this construction, force applied to the press knob 232 against the bias of the springs 240 is effective to move the operator button 224 to the release position at which the locking pin 230 is withdrawn from the upper and lower apertures 214,216. In an opposite fashion, when force is withdrawn from the press knob 232, the springs 240 are effective to move the operator button 224 to the locking position at which the locking pin 230 is again within the projected region of the upper and lower apertures 214, 216.

The stop ring 208 is also provided with a pair of aligned master bores 242 through the upper and lower walls 210, 212, although only master bore 242 through upper wall 210 is illustrated. The master bores 242 are coincident with, or overlie, the internal cavity 220. The tongue 226 of the operator button 224 has a slave bore 244 therethrough which is elongated in the direction of movement of the operator button relative to the stop ring 208. The slave bore 244 is aligned with the master bores 242 when the tongue 226 is fully received in the internal cavity 220. A master pin 246 is fittingly received in the master bores 242 and is slidably received through the slave bore 244. Thus, when fully assembled, the stop member 206 is of a unitary construction and the operator button 224 is limited to movement on the stop ring between the locking position and the release position as just described.

A modified stop member 248 is illustrated in FIG. 22. It includes a stop ring 250 and a central aperture 252 for slidable reception of the stop ring on the shaft 146. A peripheral wall 254 is recessed as at 256 for reception of an operator screw 258 which is threadedly received in a threaded bore 260. Rotation of the operator screw 258 is selectively effective to cause an integral locking pin 262 to be projected into the central aperture when the operator screw is in the advanced position and being withdrawn from the central aperture when the operator screw is in the inactive position. As with the locking pin 230, the locking pin 262 is engagable with a selected one of the plurality of the stop holes 200 in the shaft 146.

Another modified stop member 264 is illustrated in FIG. 23. It is of a construction similar to the stop member 248 in that it has a stop ring 266 and a central aperture 268 for slidable reception of the stop ring on the shaft 146. Also, a peripheral wall 270 is recessed as at 272 to accommodate an operator screw 274 which is threadedly received in a threaded bore thereof. In this instance, the operator screw 274 has a blunt end surface 276 facing the central aperture 268 for engagement with the shaft 146 when the operator screw is in the advanced position and being withdrawn from the central aperture and spaced from the shaft 146 when the operator screw is in the inactive position.

Figures 24, 25:
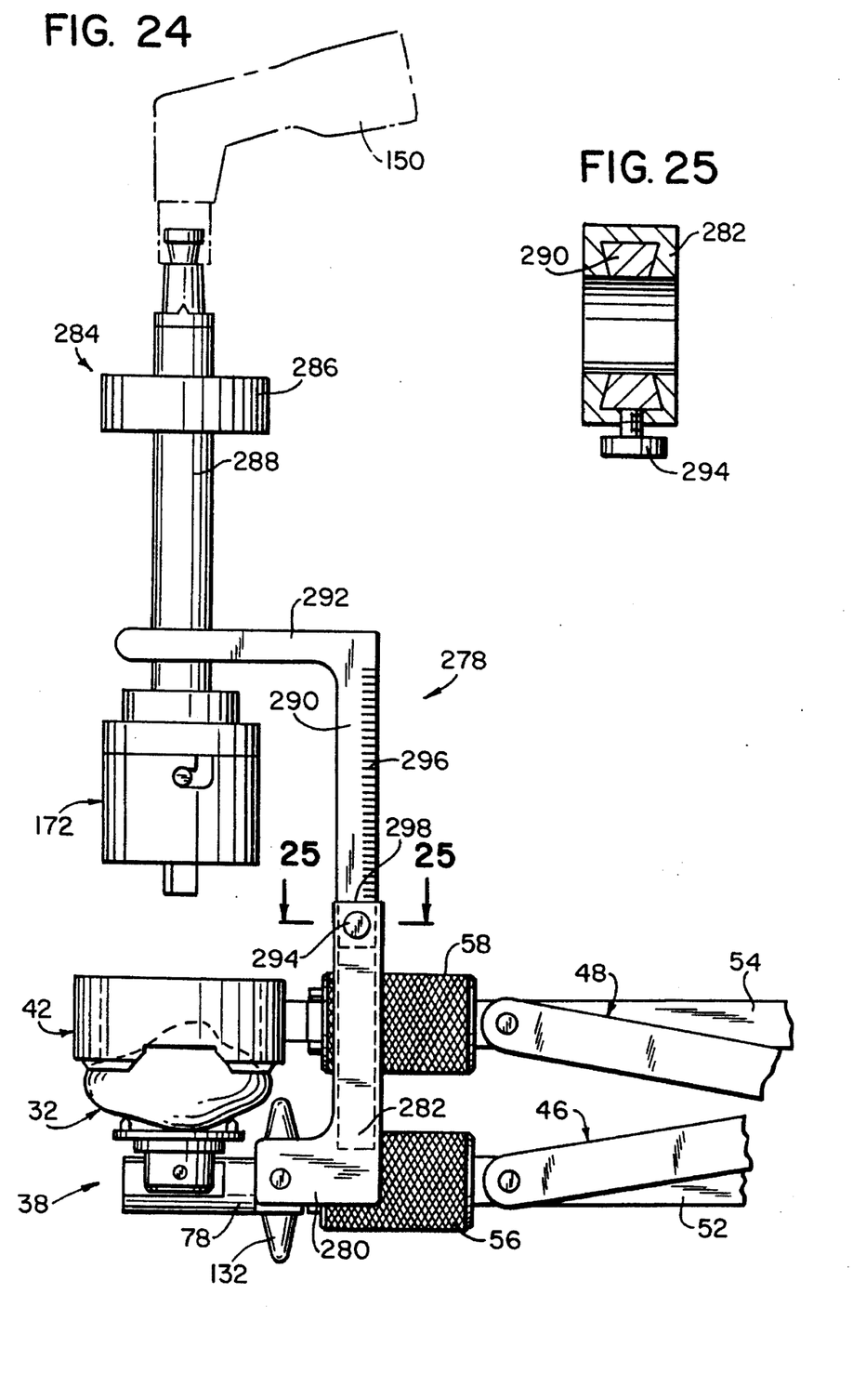
FIG. 24 is a detail side elevation view, similar to FIG. 9, illustrating another embodiment of the invention.
FIG. 25 is a cross-section view taken generally along line 25—25 in FIG. 24.

Turn now to FIGS. 24 and 25 for a modified construction of depth gauge tower 278. The tower 278 has a base member 280 which is releasably fixed to the mounting finger 78 of the jaw mechanism 38 in a manner similar to that previously described with respect to the tower 118. A lower body member 282 is integral with the base member 280 and upstanding therefrom and is spaced from the modified reamer assembly 284. The reamer assembly 284 differs from the reamer assembly 136 in that a stop member 286 is fixed on a reamer shaft 288 and is not adjustable in the manner of the stop assembly 198.

An upper body member 290 is telescopingly mounted on the lower body member 282 for selective movement between a lowered position and a raised position. This telescoping construction is generally illustrated in FIG. 25. A pair of integral spaced apart substantially parallel prong arms 292 extend transversely from an upper end of the upper body member 290, that is, at a location distant from the lower body member 282.

As previously mentioned, the height of the upper body member 290 with respect to the lower body member 282 is adjustable and when a desired relative positioning has been achieved, a locking screw 294 threaded on the lower body member 282 is tightened to engage the upper body member 290 to hold it fast. A plurality of graduated indicia 296 is formed on the upper body member 290 at longitudinally spaced locations for indicating the relative positioning between the members 282, 290. In actual fact, when a specific one of the indicia 296 is aligned with a marker edge 298, being a terminal upper edge of the lower body member 282, that specific item of indicia indicates the specific size of the natural patella to be reconstructed. The apparatus comprising the reamer assembly 284 and the depth gauge tower 278 is so constructed that when such an item of indicia has been selected, a specific depth of resection will be achieved by the cutter blades 154, 156 and by the cutting blades 178,180 when the stop member 286 has come into engagement with the prong arms 292 such that the predetermined depth of resection of the patella is substantially equal to the thickness of the selected patellar prosthesis. Thus, in this instance, the adjustment is in the tower 278 itself and not in the reamer assembly 284 as in the previously described embodiment.

While preferred embodiments of the invention have been disclosed in detail, it should be understand by those skilled in the art that various other modifications may be made to the illustrated embodiments without departing from the scope of the invention as described in the specification and defined in the appended claims.

What is claimed is:

1. A system for preparing a natural patella for implantation thereon of a patellar prosthesis having a fixation surface and fixation means projecting from the fixation surface, said system comprising:

support means for holding the patella stationary;

reamer means for simultaneously resecting a posterior side of the patella as it is held by said support means to form a prosthesis receiving surface for reception thereon of the fixation surface of the patellar prosthesis and forming a mounting bore therein for reception of the fixation means of the patellar prosthesis, said reamer means being movable between a first position spaced from the posterior surface of the patella and a second position at which formation of both the receiving surface and of the mounting bore therein has been completed, said reamer means including:

an elongated shaft extending between a driving end for attachment to driver means and a driven end distant from said driving end;

bore cutting means on said driven end for forming the mounting bore to accept the prosthesis;

a patella basket releasably fixed to said driven end of said elongated shaft, said patella basket including a cylindrical sidewall releasably attached to said elongated shaft, a bottom wall, and resection cutting blades integral with said bottom wall, said bottom wall having a plurality of first openings associated with said cutting blades to receive therethrough bone material excised from the patella upon operation of said reamer means and second openings for reception therethrough of said bore cutting means;

said bore cutting means including cutting blades projecting through the second openings in said bottom wall and extending away from said bottom wall;

stop means on said reamer means engageable with said support means when said reamer means reaches said second position such that the predetermined depth of resection of the patella is substantially equal to the thickness of the selected patellar prosthesis; and guide means for guiding said reamer means as it moves between said first and second positions.

2. A patella preparation system as set forth in claim 1 wherein said reamer means includes a plurality of transversely extending, longitudinally spaced stop holes in said shaft; and wherein said stop member includes:

a stop ring having upper and lower spaced walls with aligned upper and lower central apertures therein for slidable reception on said shaft and a peripheral wall joining said upper and lower walls, said upper, lower and periperal walls defining an internal cavity, said peripheral wall having an opening into the internal cavity;

an operator button including a tongue adapted for slidable reception into the internal cavity, said tongue having a central bore therethrough coincident with the upper and lower apertures in said upper and lower walls when said tongue is fully received in the internal cavity and a locking pin projecting into the central bore, said operator button being movable between a locking position at which the central bore is coincident with the upper and lower apertures in said upper and lower walls and a release position at which said locking pin is not coincident with the upper and lower apertures, said locking pin being selectively receivable in any one of the stop holes; and resilient means biasing said operator button toward said locking position.

3. A patella preparation system as set forth in claim 2 wherein said operator button includes a press knob integral with said tongue having a pair of spaced spring engaging surfaces;

wherein said stop ring has a pair of spaced apart spring receiving bores in said peripheral wall generally aligned with said spring engaging surfaces; and wherein said resilient means includes a pair of compression springs received, respectively, in the spring receiving bores;

whereby, force applied to said press knob against the bias of said springs is effective to move said operator button to said release position; and whereby, withdrawal of force applied to said press knob is effective to permit said springs to move said operator button to said locking position.

4. A patella preparation system as set forth in claim 2 wherein said stop ring has a pair of aligned master bores through said upper and lower walls and coincident with the internal cavity;

wherein said tongue has a slave bore therethrough which is elongated in the direction of movement thereof, the slave bore being aligned with the master bores; and including:

a master pin fittingly received in the master bores and slidably received through the slave bore;

whereby, said operator button is limited to movement on said stop ring between said locking position and said release position.

5. A patella preparation system as set forth in claim 1 wherein said stop means includes:

a stop ring having upper and lower walls, a central aperture extending between said upper and lower walls for slidable reception of said stop ring on said shaft, and a peripheral wall joining said upper and lower walls, said periperal wall having a threaded bore opening into the central aperture; and an operator screw threadedly received in the threaded bore and movable between advanced and retracted positions, said operator screw including a locking pin projecting into the central aperture when said operator screw is in the advanced position and being withdrawn from the central aperture when said operator screw is in the inactive position, said locking pin being engageable with a selected one of the stop holes.

6. A patella preparation system as set forth in claim 1 wherein said stop means includes:

a stop ring having upper and lower walls, a central aperture extending between said upper and lower walls for slidable reception of said stop ring on said shaft, and a peripheral wall joining said upper and lower walls, said periperal wall having a threaded bore opening into the central aperture; and an operator screw threadedly received in the threaded bore and movable between advanced and retracted positions, said operator screw including a blunt end surface facing the central aperture for engagement with said shaft when said operator screw is in the advanced position and being withdrawn from the central aperture and spaced from said shaft when said operator screw is in the retracted position.

7. A system for preparing a natural patella for implantation thereon of a patellar prosthesis having a fixation surface and fixation means projecting from the fixation surface, said system comprising:

support means for holding the patella stationary;

reamer means for simultaneously resecting a posterior side of the patella as it is held by said support means to form a prosthesis receiving surface for reception thereon of the fixation surface of the patellar prosthesis and forming a mounting bore therein for reception of the fixation means of the patellar prosthesis, said reamer means being movable between a first position spaced from the posterior surface of the patella and a second position at which formation of both the receiving surface and of the mounting bore therein has been completed;

stop means on said reamer means engageable with said support means when said reamer means reaches said second position such that the predetermined depth of resection of the patella is substantially equal to the thickness of the selected patellar prosthesis; and guide means for guiding said reamer means as it moves between said first and second positions;

a plurality of locating means on said reamer means associated, respectively, with a plurality of thicknesses of natural patellas;

a depth gauge tower mounted on said support means having a main body spaced from said reamer means and a pair of integral spaced apart substantially parallel prong arms extending transversely therefrom so as to receive said reamer means therebetween;

said stop means including a stop member releasably attachable to said reamer means at a selected one of the plurality of said locating means and engageable with said support means when said reamer means reaches said second position such that the predetermined depth of resection of the patella is substantially equal to the thickness of the selected patellar prosthesis, said stop member on said reamer means being engageable with said prong arms to prevent further movement of said reamer means when said reamer means reaches the second position.

8. A patella preparation system as set forth in claim 7 including:

a plurality of indicia means on said reamer means associated with said locating means for indicating thicknesses of patella prostheses which may be selected.

9. A patella preparation system as set forth in claim 7 wherein said reamer means includes:

an elongated shaft extending between a driving end for attachment to driver means and a driven end distant from said driver end;

first cutting means on said driven end for resecting the prosthesis receiving surface; and second cutting means on said driven end for forming the mounting bore to accept the prosthesis; and wherein said locating means include a plurality of detent members at longitudinally spaced locations along the length of said elongated shaft; and wherein said stop member includes:

a ring member having an aperture for slidably receiving said elongated shaft therein;

a pin member selectively movable between a retracted position withdrawn from the aperture and an advanced position extending into the aperture and into engagement with a selected one of said detent members; and resilient means biasing said pin member toward said advanced position.

10. A system for preparing a natural patella for implantation thereon of a patellar prosthesis having a fixation surface and fixation means projecting from the fixation surface, said system comprising:

support means for holding the patella stationary including:

first jaw means for engaging an anterior surface of the patella; and second jaw means for engaging the posterior surface of the patella, said first and second jaw means having a common axis;

reamer means for simultaneously resecting a posterior side of the patella as it is held by said support means to form a prosthesis receiving surface for reception thereon of the fixation surface of the patellar prosthesis and forming a mounting bore therein for reception of the fixation means of the patellar prosthesis, said reamer means being movable between a first position spaced from the posterior surface of the patella and a second position at which formation of both the receiving surface and of the mounting bore therein has been completed, said reamer means being movable along the common axis as said reamer means moves between said first and second positions;

stop means on said reamer means engageable with said support means when said reamer means reaches said second position such that the predetermined depth of resection of the patella is substantially equal to the thickness of the selected patellar prosthesis;

guide means for guiding said reamer means as it moves between said first and second positions; and a depth gauge tower mounted on said support means including:

a base member releasably fixed to said first jaw means;

a main body integral with said base member and spaced from said reamer means and disposed generally parallel to the common axis;

a pair of spaced apart substantially parallel prong arms integral with said main body and extending transversely therefrom so as to receive said reamer means therebetween; and wherein said reamer means includes a stop member which is engageable with said prong arms to prevent further movement of said stop means when said reamer means reaches said second position.

11. A patella preparation system as set forth in claim 10 wherein said support means includes:

a clamp handle assembly for mounting said first and second jaw means on a common axis, said first and second jaw means being movable between an open position for freely receiving the patella therebetween and a closed position in engagement with the patella to hold it stationary.

12. A patella preparation system as set forth in claim 11 wherein said clamp handle assembly includes:

a first handle for releasably mounting said first jaw means;

a second handle for releasably mounting said second jaw means;

pin means pivotally connecting said first handle and said second handle for moving said first and second jaw means between said open and closed positions; and locking means for selectively locking said first handle against movement relative to said second handle at any one of a plurality of positions.

13. A patella preparation system as set forth in claim 12 wherein said locking means includes:

a handle ratchet pivotally mounted on an end of said second handle opposite said second jaw means, said ratchet handle having a plurality of longitudinally spaced teeth thereon;

a projection member on an end of said first handle opposite said first jaw means selectively engageable with said teeth of said handle ratchet for holding said first and second handles at a desired one of the plurality of positions; and resilient means on said second handle biasing said teeth of said handle ratchet into engagement with said projection member.

14. A patella preparation system as set forth in claim 11 wherein said clamp handle assembly includes:

linkage means for moving said first and second jaw means on said common axis between the open position for freely receiving the patella therebetween and the closed position in engagement with the patella.

15. A patella preparation system as set forth in claim 14 wherein said linkage means includes:

a first link including a first connector for releasably mounting said first jaw means;

a first handle pivotally connected at one end to said first link adjacent said first connector;

a second link including a second connector for releasably mounting said second jaw means;

a second handle pivotably connected at one end to said second link adjacent said second connector, said second link being pivotally and translationally connected at opposite end to said first handle;

said first link being pivotally and translationally connected at an opposite end to said second handle; and locking means for selectively locking said first handle against movement relative to said second handle at any one of a plurality of positions.

16. A patella preparation system as set forth in claim 15 wherein said locking means includes:

a handle ratchet having a plurality of longitudinally spaced teeth pivotally mounted on an end of said second handle opposite said second jaw means;

a projection member on an end of said first handle opposite said first jaw means selectively engageable with said teeth of said handle ratchet for holding said first and second handles at a desired position; and resilient means on said second handle biasing said teeth of said handle ratchet into engagement with said projection member.

17. A patella preparation system as set forth in claim 15 wherein said first jaw means includes:

a first mounting finger including a mounting end for selective insertion into said first connector for releasable attachment thereto;

a mounting block integral with said first mounting finger at an end opposite said mounting end;

a support plate having a mounting surface and being pivotally mounted on said mounting block; and a plurality of gripping members projecting from said mounting surface for gripping engagement with the anterior surface of the patella;

wherein said second jaw means includes:

a second mounting finger including a mounting end for selective insertion into said second connector for releasable attachment thereto;

an annular bushing integral with said second mounting finger at an end opposite said mounting end, said bushing having an engagement surface;

a plurality of gripping members projecting from said engagement surface for gripping engagement with the posterior surface of the patella.

18. A patella preparation system as set forth in claim 10 wherein said depth gauge tower main body includes fixed to said first jaw means and a lower body member with said base member and spaced from and an upper body member mounted on said lower body member for selective movement between a lowered position and a raised position;

a plurality of graduated indicia on said upper body member at longitudinally spaced locations for indicating the relative positioning between said upper body member and said lower body member;

marker means on said lower body member for indicating a specific one of said indicia representing a specific relative positioning between said upper and lower body members;

each of said plurality of indicia indicating a specific depth of resection which would be achieved by said reamer means when said stop member is engageable with said prong arms, such that the predetermined depth of resection of the patella is substantially equal to the thickness of the selected patellar prosthesis.

* * * * *

UNITED STATES PATENT AND TRADEMARK OFFICE
CERTIFICATE OF CORRECTION

PATENT NO. : 5,536,271
DATED : July 16, 1996
INVENTOR(S) : Daly et al.

It is certified that error appears in the above-identified patent and that said Letters Patent is hereby corrected as shown below:

In col. 16, claim 18, lines 41, through 42, the words "fixed to said first jaw means and" should be deleted.

In col. 16, claim 18, lines 42, through 43, the words "with said base member and spaced from" should be deleted.

Signed and Sealed this

First Day of October, 1996

Attest:

BRUCE LEHMAN

Attesting Officer

Commissioner of Patents and Trademarks